United States Patent [19]

Nonogaki et al.

[11] Patent Number: 4,565,768

[45] Date of Patent: Jan. 21, 1986

[54] PHOTOSENSITIVE AZIDE COMPOSITION WITH ALKALI SOLUBLE POLYMER AND PROCESS OF USING TO FORM RESIST PATTERN

[75] Inventors: Saburo Nonogaki, Tokyo; Michiaki Hashimoto, Yono, both of Japan

[73] Assignee: Hitachi Chemical Company, Ltd., Tokyo, Japan

[21] Appl. No.: 615,749

[22] Filed: May 31, 1984

[30] Foreign Application Priority Data

Jun. 1, 1983 [JP] Japan ................................. 58-95650

[51] Int. Cl.[4] .................... G03C 1/52; G03C 1/71; G03F 7/26

[52] U.S. Cl. .................................... 430/197; 430/194; 430/325; 430/927; 260/349

[58] Field of Search ............... 430/197, 194, 325, 927; 260/349

[56] References Cited

U.S. PATENT DOCUMENTS

| | | | |
|---|---|---|---|
| 2,940,853 | 6/1960 | Sagura et al. | 430/197 |
| 3,539,559 | 11/1970 | Ruckert | 430/197 |
| 3,595,656 | 7/1971 | Ruckert et al. | 430/197 |
| 3,749,713 | 7/1973 | Clecak et al. | 260/349 |
| 4,356,247 | 10/1982 | Aotani et al. | 430/197 |
| 4,407,927 | 10/1983 | Kamoshida et al. | 430/197 |

FOREIGN PATENT DOCUMENTS 51-01444  1/1976  Japan .................................. 260/349

OTHER PUBLICATIONS

Partial English Translations of Japanese Patent Publication No. 45-22082.
Partial English Translation of Japanese Patent Publication No. 53-34902.

*Primary Examiner*—Charles L. Bowers, Jr.
*Attorney, Agent, or Firm*—Antonelli, Terry & Wands

[57] ABSTRACT

A photosensitive composition comprising an equimolar condensation product of an aromatic azide compound having an aldehyde group and isophorone, and an alkali-soluble polymeric compound is a negative-type photoresist with a high resolution suitable for the fabrication of semiconductor devices.

8 Claims, 6 Drawing Figures

PHOTOSENSITIVE AZIDE COMPOSITION WITH ALKALI SOLUBLE POLYMER AND PROCESS OF USING TO FORM RESIST PATTERN

BACKGROUND OF THE INVENTION

This invention relates to a photosensitive composition, and more particularly to a photoresist with a high resolution suitable for fabrication of semiconductor devices.

For improving the performance of semiconductor devices such as IC, LSI, etc., finer processings are necessary, and thus a particularly higher resolution is required for the photoresist for use in the processing.

Photoresists can be classified into two groups, i.e. a positive type which becomes soluble in solvents by light exposure and a negative type which becomes insoluble in solvents by light exposure. Most of the positive type photoresists for use in the fabrication of semiconductor devices are mixtures of an alkali-soluble phenolic resin as a film-forming constituent with a naphthoquinonediazide derivative as a photo-sensitive constituent. Most of the negative type photoresists for use in the fabrication of semi-conductor devices are mixtures of cyclized rubber with an aromatic bisazide as a photosentive constituent.

Comparison of the resolution of the two groups of photoresists reveals that the positive type photoresist has a higher resolution than the negative type photoresist, and consequently positive type photoresists recently are more often used in the fabrication of high performance semiconductor devices.

The reasons why the positive type photoresist has a higher resolution than the negative type photoresist are that;
(1) the positive type photoresist has a higher contrast than the negative type photoresist, and
(2) the positive type photoresist can be developed without any swelling in a developer, whereas the negative type photoresist swells in a developer and its pattern sometimes may get out of shape or may be deformed.

Even in the case of negative type photoresists, a higher resolution can be expected, if it can have a higher contrast and exhibits no swelling in a developer.

It is known among the photoresists for use in other fields than the fabrication of semiconductor devices that there are negative type photoresist which shows no swelling in a developer. For example, it is well known that a mixture of an alkali-soluble phenolic resin with an aromatic azide is applicable as a negative type photoresist for photolithography, and this photoresist has no swelling phenomenon when developed in an aqueous alkaline solution. Japanese Patent Publication No. 45-22082 discloses a negative type photoresist containing an aromatic azide compound and an alkali-soluble phenol-formaldehyde resin, and Japanese Patent Publication No. 53-34902 discloses a negative type photoresist containing an aromatic azide compound and polymers of hydroxystyrene.

However, no cases have been found, where these photoresists are used in the fabrication of semiconductor devices, because it seems that these photoresists have been developed mainly for the photolithographic application, and are suitable for application as a film having a thickness of several ten microns, and are not always suitable for application as a film having a thickness of from less than one micron to a few microns as in the fabrication of semiconductor devices.

SUMMARY OF THE INVENTION

An object of the present invention is to provide a negative type photoresist with a high resolution, and this and other objects can be attained by a photosensitive composition which comprises an equimolar condensation product of an aromatic azide compound having an aldehyde group and isophorone, and an alkali-soluble polymeric compound.

DETAILED DESCRIPTION OF PREFERRED EMBODIMENTS

Figure 1:
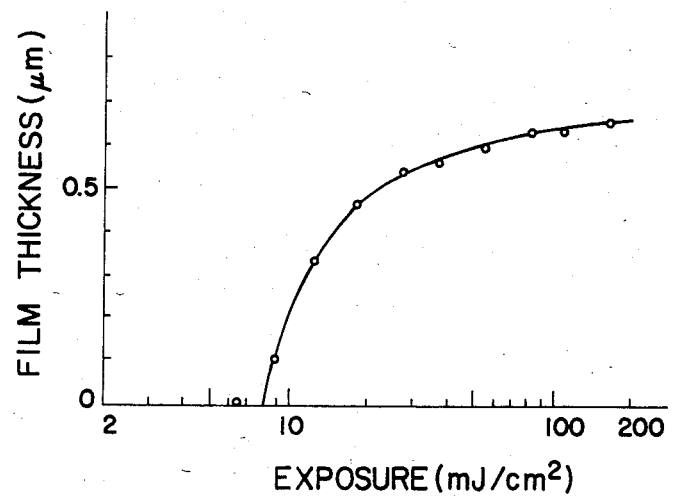
FIGS. 1, 3 and 5 are diagrams showing exposure characteristics of photosensitive compositions according to the present invention.

A precaution for utilizing a mixture of alkali-soluble polymers with an aromatic azide as a negative type photoresist in the fabrication of semiconductor devices is that the photoresist is used as a film having a thickness of from less than one micron to a few microns, as mentioned above. Even in such a thin film, insolubilization takes place with a high efficiency by light exposure, and to prevent a decrease in exposed image quality due to light reflection (halation) from the substrate as a support for the film, it is necessary that the aromatic azide in the film can intensively absorb the reflected light.

In the fabrication of semiconductor devices, a superhigh pressure mercury lamp is often used as a light source for light exposure to photoresists. The light from the light source includes much ultraviolet light with a wavelength centering at 365 nm. Thus, it is desirable that the photosensitive constituent of the photoresists for use in this application can intensively absorb the light with the wavelength of 365 nm and cause a photochemical reaction, and furthermore can be contained at a high concentration in the photoresists.

Usually, the photoresist is dissolved in an appropriate organic solvent and handled in the form of a solution. Thus, it is necessary that the aromatic azide that must be contained at a high concentration in the photoresist must be also soluble at a high concentration in the solvent for the photoresist.

In summary, it is desirable that the photosensitive constituent of negative type photoresist suitable for the fabrication of semiconductor devices is readily soluble in a solvent for the photoresist and can intensively absorb the light with the wavelength of 365 nm in the photoresist film.

The present inventors have made extensive studies on the basis of this conclusion, and have succeeded in synthesis of novel aromatic azides that can satisfy the foregoing conditions thoroughly and have obtained a negative type photoresist with a high resolution suitable for the fabrication of semiconductor devices by utilizing those aromatic azides.

The present photosensitive composition is characterized by containing an equimolar condensation product of an aromatic azide compound having an aldehyde group and isophorone, and an alkali-soluble polymeric compound.

The amount of the azide compound as the condensation product is preferably 5–40% by weight, and more preferably 10–30% by weight on the basis of the polymeric compound. Below 5% by weight, the sensitivity is deteriorated, whereas above 40% by weight, the film characteristics are deteriorated.

The aromatic azide compound for forming a condensation product includes, for example, azidobenzaldehyde, azidocinnamaldehyde, etc.

The condensation product obtainable from these compounds includes, for example, 3-(4'-azidostyryl)-5,5-dimethyl-2-cyclohexene-1-one, 3-(4-p-azidophenyl-1,3-butadienyl)-5,5-dimethyl-2-cyclohexene-1-one, etc., where the first condensation product can include compounds having the azide group not only at position 4', but also at position 2' or 3', and the second condensation product can include compounds having the azide group not only at position p, but also at position m or o.

The polymeric compound is preferably those having a phenolic hydroxyl group, for example, polymers and copolymers of hydroxystyrene, or their partially modified polymers, condensation products of phenols and formaldehyde, etc.

The developer includes an aqueous solution of sodium silicate, an aqueous solution of trisodium phosphate, etc.

The present invention will be described in detail below, referring to Examples.

First of all, synthesis of novel condensation product of an aromatic azide will be given below:

9.0 g of isophorone and 10.0 g of p-azidobenzaldehyde were placed in a 100-ml glass beaker, and mixed, and then, a solution of 0.26 g of potassium hydroxide in 40 g of methanool was added thereto. The mixture was stirred to obtain a homogeneous solution. Then, the solution was left standing in the dark place for 6 days. Yellow needle crystal deposited in the solution was separated from the mother liquid by filtration, and washed with methanol. Then, the methanol on the crystal was evaporated off at room temperature, whereby 7.4 g of yellow crystal was obtained. As a result of elementary analysis and NMR spectrum measurement, it was found that the crystal was a compound having the following structural formula [I], i.e. 3-(4'-azidostyryl)-5,5-dimethyl-2-cyclohexene-1-one:

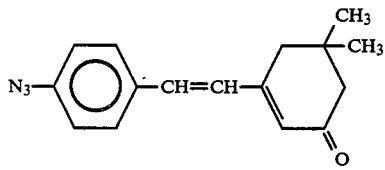
[I]

This compound will be hereinafter referred to as "Azide I". Melting point of this compound was 107°–108° C. and its analytical data are: 72.17% C, 6.45% H and 15.26% N (calculated values are: 71.89% C, 6.41% H, and 15.72% N).

As a result of light absorption spectrum measurement with a UV. visible spectrophotometer, it was found that the maximum absorption of Azide I in methanol was at the wavelength of 346 nm, and the molecular absorption coefficient at this point was $4.2 \times 10^4$ mole$^{-1}$·l·cm$^{-1}$.

Results of measuring solubilities of various aromatic azides in solvents are given below.

Solubilities of azide I, 4-azido-4'-methoxychalcone having the following structural formula [II] (which will be hereinafter referred to as "azide II") and 2,6-bis(4'-azidobenzylidene)cyclohexanone having the following structural formula [III] (which will be hereinafter referred to as "azide III") in isoamyl acetate, methylcellosolve acetate, cyclohexanone and diacetone alcohol were investigated.

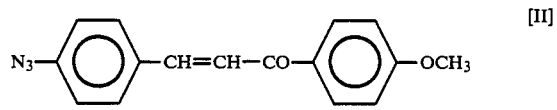
[II]

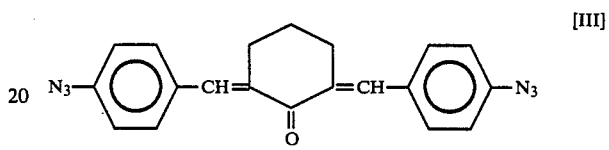
[III]

That is, each of the azides was dissolved in each solvent to its saturation at 20° C., and a small amount (0.2–0.7 g) of the solution was weighed out onto a dish made of an aluminum foil. After evaporation of the solvent, the weight of the azide remaining on the dish was measured, and the concentration of azide in the solution was determined from the measured weight and the weight of the initial weighed-out solution.

Weight percentages of the observed azides are given in the following Table.

TABLE

| solvent azide | isoamyl acetate | methyl-cellosolve acetate | cyclo-hexanone | diaceton alcohol |
|---|---|---|---|---|
| azide I | 5.3 wt % | 6.3 wt % | 16.9 wt % | 5.2 wt % |
| azide II | 1.9 wt % | 3.6 wt % | 8.3 wt % | 1.9 wt % |
| azide III | 0.7 wt % | 0.7 wt % | 2.3 wt % | 1.4 wt % |

Azide II is selected from the known aromatic azides used as a photosensitive constituent for the photoresist as typical of those having a relatively high solubility in the solvents.

Azide III is known as aromatic azide for use in the cyclized rubber-azide negative type photoresist. The solvents selected for the investigation are the ones that seem to be appropriate for photoresist.

When a mixture of an alkali-soluble polymer and an aromatic azide is used as a photoresist for the fabrication of semiconductor devices, it is desirable that a ratio by weight of the azide to the polymer is at least 0.2:1 and an appropriate concentration of the polymer in the photoresist solution is about 20% by weight. Thus, it is desirable that a concentration of the azide in the photoresist solution is at least 4% by weight.

It is seen from the foregoing Table that Azide I satisfies the desired condition when dissolved in all of the solvents listed in the foregoing Table, whereas Azide II satisfies the condition only when dissolved in cyclohexanone, and Azide III fails to satisfy the condition when dissolved in each of the solvents listed in the foregoing Table.

EXAMPLE 1

A photoresist solution having the following composition was prepared.

| | |
|---|---|
| Homopolymer of p-hydroxystyrene (Maruzen Resin M from Maruzen Oil Co., Japan) | 16 parts by weight |
| Azide I | 4 parts by weight |
| Methylcellosolve acetate | 80 parts by weight |

The solution was spin-coated onto a 3-inch silicon wafer at 3,000 rpm and heated in air at 80° C. for 10 minutes. Light from a 500-W super-high pressure mercury lamp was passed through Toshiba glass filter UV-D2 to eliminate short wavelength ultraviolet light and visible light therefrom and allowed to hit the photoresist film on the wafer patternwise while changing the exposure time and exposed positions. After the exposure, the photoresist film was developed in an aqueous 0.95% tetramethylammonium hydroxide solution as a developer at 20° C. for 1.5 minutes, whereby the photoresist film on the unexposed parts were removed by dissolution, while only the photoresist film insolubilized by the exposure remained on the wafer. No evidence of swelling by the developer was observed at all on the photoresist film during or after the development. The thickness of photoresist film after the development was measured by an interference microscope, and plotted against the exposure to obtain an exposure characteristic curve of the photoresist. The light intensity was measured by a calibrated thermocouple, and the exposure was obtained as a product of the measured light intensity and exposure time. The thus obtained exposure characteristic curve is shown in FIG. 1.

Figure 2:
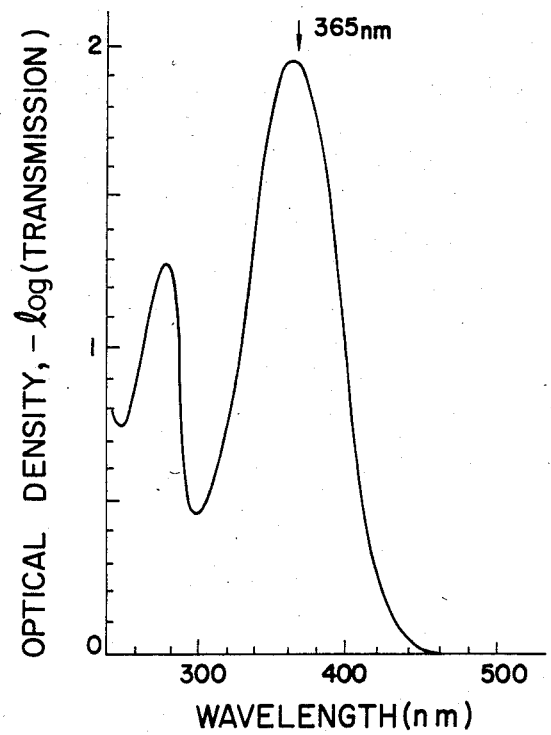
FIGS. 2 and 6 are diagrams showing light absorption spectra of photosensitive compositions according to the present invention.

Results of measuring a light absorption spectrum of the photoresist film having the thickness of 0.66 μm are shown in FIG. 2.

EXAMPLE 2

A photoresist solution having the following composition was prepared:

| | |
|---|---|
| Phenol-formaldehyde resin (Alnovol PN 430 from Hoechst) | 16 parts by weight |
| Azide I | 4 parts by weight |
| Methylcellosolve acetate | 80 parts by weight |

Figure 3:
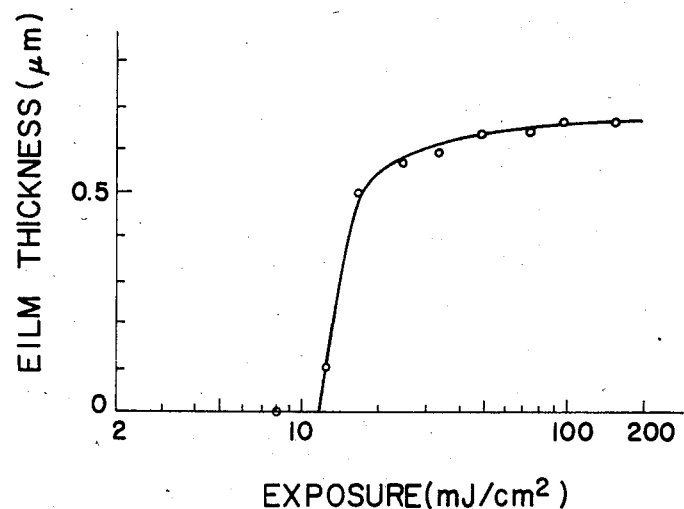

The solution was coated onto a silicon wafer, heated and exposed to light in the same manner as in Example 1. The photoresist film after the exposure was developed in an aqueous 3.3% tetramethylammonium hydroxide solution as a developer at 20° C. for 3 minutes. Furthermore, an exposure characteristic curve of the photoresist was obtained in the same manner as in Example 1. In this example, no swelling of the photoresist film by the developer was also observed at all. The thus obtained exposure characteristic curve is shown in FIG. 3.

COMPARATIVE EXAMPLE

A photoresist solution having the following composition was prepared.

| | |
|---|---|
| Homopolymer of p-hydroxystyrene (Maruzen Resin M from Maruzen Oil Co., Japan) | 16 parts by weight |
| Azide II | 3.2 parts by weight |
| Cyclohexanone | 80.8 parts by weight |

Figure 4:
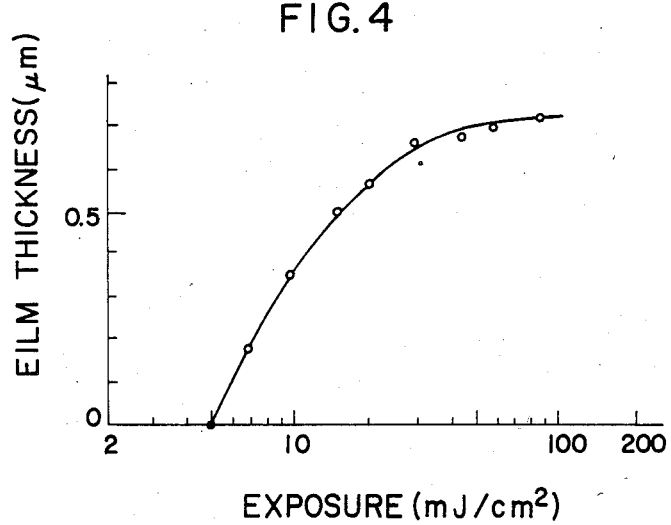
FIG. 4 is a diagram showing photosensitive characteristics of a photosensitive composition used as a comparative example.

An exposure characteristic curve of the photoresist was obtained from the solution in the same manner as in Example 1 and is shown in FIG. 4.

As shown in the foregoing Table, Azide I of the present invention has a considerably better dissolution characteristic than the two azides used for comparison. That is, various kinds of organic solvents can be used as solvents for the photoresist by using Azide I as a photosensitive constituent, and a range of solvent selection can be considerably broadened. Even if it is required to increase the concentration of aromatic azide in a photoresist solution to an extremity in a special application, for example, when a particularly high sensitivity is required, such a requirement can be satisfied by using Azide I and cyclohexanone.

It is seen from FIG. 2 that the photoresist using Azide I can intensively absorb the light with a wavelength of about 365 nm. In this case, the polymeric contituent hardly absorbs the light, and thus it is seen that the light absorption is carried out principally by Azide I. Thus, it is seen that Azide I has a practically very preferable photospectrosensitivity characteristic.

It is seen from FIGS. 1 and 3 that the photoresists disclosed in Examples 1 and 2 have a practically high sensitivity and a distinguished contrast characteristic. Although the photoresist shown in Comparative Example has a sensitivity as high as that of the photoresists of the present invention, it has a lower contrast. This can be seen from the curve gradient in FIG. 4 which is smaller than those in FIGS. 1 and 3. Thus, it will be appreciated that the photoresists disclosed in Examples 1 and 2 have a distinguished high-contrast characteristic, as compared with the photoresist disclosed in Comparative Example, and have likewise a distinguished high-resolution capability.

Even if the position of azido group of Azido I is changed from position 4' to position 3' or 2', the photospectrosensitivity characteristic of the resulting compound is not changed, and its solubility in solvents is not lowered. Thus, the usefulness as a photosensitive constituent for the negative type photoresist is not changed.

As the alkali-soluble polymers to be mixed with Azide I and said 3'-and 2'-azide isomers, homopolymers or copolymers of hydroxystyrenes or their partially modified polymers, various phenol-formaldehyde condensation products and various cresol-formaldehyde condensation products, etc. can be applied besides the polymers used in Examples 1 and 2.

Furthermore, the aromatic azide of the present invention can be used in a mixture with other aromatic azides.

Synthesis of another condensation product of an aromatic azide will be given below:

1.4 g of isophorone and 1.7 g of p-azidocinnamaldehyde were mixed with 10 ml of methanol, and a solution of 0.04 g of sodium hydroxide in 1 ml of water was added thereto to obtain a homogeneous solution. The solution was left standing overnight, and the deposited precipitates were separated by filtration from the mother liquid, whereby 1.1 g of crystal was obtained. By recrystallization from methanol, needle crystal having a melting point of 142.0°–143.5° C. was obtained. Its absorption spectra measured in methanol had the longest wavelength absorption maximum at 368 nm and the molecular absorption coefficient at that wavelength was $5.3 \times 10^4 \, l \cdot mol^{-1} \cdot cm^{-1}$. NMR spectra were measured in deutriated chloroform with TMS as the internal standard. As a result, spectra with absorptions at 1.09 ppm (six methyl protons), 2.28 ppm (two methylene protons), 2.40 ppm (two methylene protons), 6.0 ppm (one olefinic proton), 6.5–7.0 ppm (four olefinic protons), 7 ppm (doublet, two p-disubstituted benzene ring protons) and 7.45 ppm (doublet, two p-disubstituted benzene ring protons) were obtained. From these results, it was confirmed that the crystal was a compound having the following structural formula [IV], i.e. 3-(4-azidophenyl-1,3-butadienyl)-5,5-dimethyl-2-cyclohexene-1-one. The compound will be hereinafter referred to as "Azide IV".

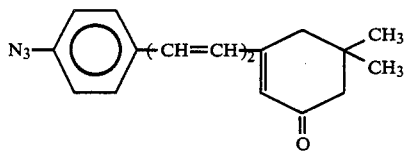
[IV]

EXAMPLE 3

A photoresist solution having the following composition was prepared.

| | |
|---|---|
| Homopolymer of p-hydroxystyrene (Maruzen Resin M from Maruzen Oil., Japanese) | 20 parts by weight |
| Azide IV | 4 parts by weight |
| cyclohexanone | 80 parts by weight |

The solution was spin-coated onto a 3-inch silicon wafter at 3,000 rpm and heated in air at 80° C. for 20 minutes. Light from a 500-W super-high pressure mercury lamp was passed through Toshiba glass filter UV39 or V-Y43 to eliminate short wavelength ultraviole light therefrom and allowed to hit the photoresist film on the wafer patternwise while changing the exposure time and exposure positions. After the exposure, the photoresist film was developed in an aqueous 0.95% tetramethylammonium hydroxide solution at 20° C. for 25 minutes, whereby the photoresist film at the unexposed parts were removed by dissolution, while only the photoresist film insolubilized by the exposure remained on the wafer. In this case, no swelling of the photoresist film by the developer was observed. The thickness of the photoresist film after the development was measured by an interference microscope, and plotted against the exposure to obtain an exposure characteristic of the photoresist. The exposure was determined in the same manner as in Example 1. The obtained exposure characteristic is shown in FIG. 5, where an exposure characteristic of commercially available positive type photoresist (OFPR-800 from Tokyo Ohka Kogyo Co., Japan) measured under the same exposure conditions is also shown.

Figure 6:
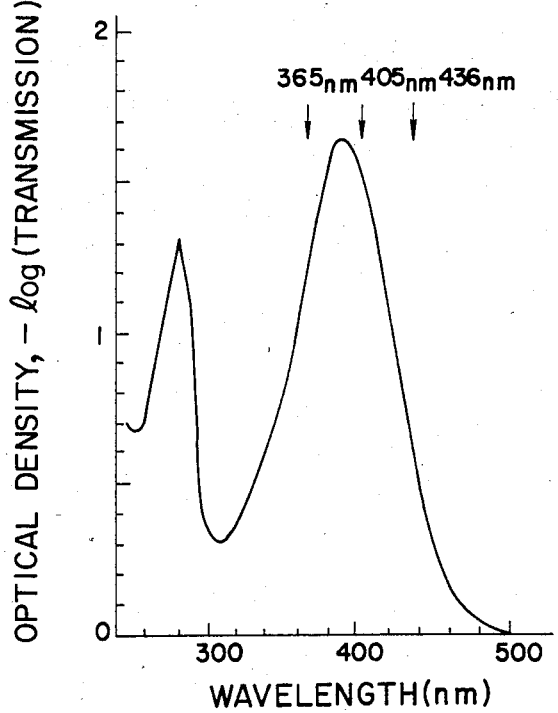

Results of measuring light absorption spectra of the photoresist film having the thickness of 0.72 μm are shown in FIG. 6, from which it is seen that the photoresist using Azide IV can intensively absorb the light at the wavelength of about 390 nm. With a super-high pressure mercury lamp as a light source, the photoresist has a preferable photospectrosensitivity characteristic corresponding to line spectra of the mercury lamp at the wavelengths of 365 nm, 405 nm, and 436 nm.

Figure 5:
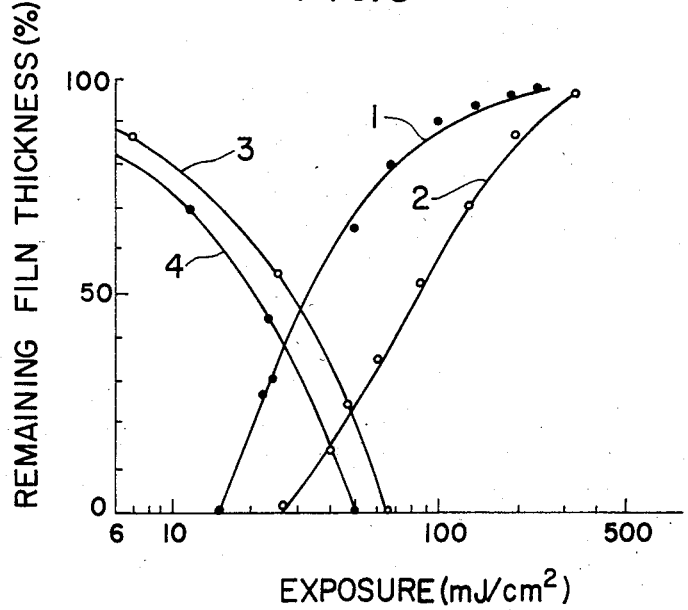

As is apparent from FIG. 5, the photoresist of this Example is a negative type photoresist having a practically high sensitivity to the light of super-high pressure mercury lamp at 405 nm and 436 nm. In FIG. 5, curves 1 and 2 show exposure characteristics of the photoresist of the present invention (filter used: 1: Toshiba UV39 and 2: Toshiba V-Y43), whereas curves 3 and 4 show exposure characteristics of OFPR-200 (filter used: 3: Toshiba V-Y43 and 4: Toshiba UV39).

Isomers having the azido group at positions o and m had substantially equal results.

As is clear from the foregoing description, the present photosensitive composition comprising an alkali-soluble polymeric compound and the azide compound provides a negative type photoresist with a high sensitivity and a high resolution particularly suitable for the fabrication of semiconductor devices.

What is claimed is:

1. A photosensitive composition which comprises an admixture of a photosensitive condensation product of equimolar amounts of isophorone and an aromatic azide compound having an aldehyde group, and an alkali-soluble polymeric compound, the amount of the condensation product being 5–40% by weight on the basis of the polymeric compound.

2. A photosensitive composition according to claim 1, wherein the condensation product is at least one member selected from the group consisting of 3-(azidostyryl)-5,5-dimethyl-2-cyclohexene-1-one and 3-(4-azidophenyl-1,3-butadienyl)-5,5-dimethyl-2-cyclohexene-1-one.

3. A photosensitive composition according to claim 1 or claim 2, wherein the polymeric compound is at least one member selected from the group consisting of condensation product of a phenol and formaldehyde, and hydroxystyrene polymer.

4. A photosensitive composition which comprises an admixture of
(i) a condensation product of equimolar amounts of isophorone and at least one azide compound selected from the group consisting of an azidobenzaldehyde and an azidocinnamaldehyde; and
(ii) an alkali-soluble polymeric compound; the amount of the condensation product being 5 to 40% by weight on the basis of the polymeric compound.

5. A photosensitive composition according to claim 4, wherein the condensation product is at least one member selected from the group consisting of 3-(4'-azidostyryl)-5,5-dimethyl-2-cyclohexane-1-one and 3-(4-azidophenyl-1,3-butadienyl)-5,5-dimethyl-2-cyclohexene-1-one.

6. A photosensitive composition according to claim 4, wherein the polymeric compound is at least one member selected from the group consisting of a condensation product of a phenol and formaldehyde and a hydroxystyrene polymer.

7. A photosensitive composition according to claim 1 or claim 4, wherein the condensation product has an absorption wavelength of about 365, 405 or 436 and is highly soluble in an organic solvent.

8. A process for forming a pattern which comprises a step of coating a substrate with a photosensitive composition comprising (i) a photosensitive condensation product of equimolar amounts of isophorone and at least one azide compound selected from the group consisting of an azidobenzaldehyde and an azidocinnamaldehyde, and (ii) an alkali-soluble polymeric compound, the amount of the condensation product being 5 to 40% by weight on the basis of the polymeric compound, thereby forming a film on the substrate; a step of exposing the film to light of a predetermined pattern; and a step of developing the film with an aqueous alkali solution, thereby removing unexposed parts and forming a pattern.

* * * * *